United States Patent [19]

Vernon et al.

[11] Patent Number: 4,922,201

[45] Date of Patent: May 1, 1990

[54] EDDY CURRENT METHOD FOR MEASURING ELECTRICAL RESISTIVITY AND DEVICE FOR PROVIDING ACCURATE PHASE DETECTION

[75] Inventors: Susan N. Vernon, Annandale, Va.; Paul M. Gammell, Silver Spring, Md.

[73] Assignee: The United States of America as represented by the Secretary of the Navy, Washington, D.C.

[21] Appl. No.: 294,622

[22] Filed: Jan. 9, 1989

[51] Int. Cl.$^5$ .................... G01N 27/72; G01R 27/02; G01R 33/12

[52] U.S. Cl. .................... 324/236; 324/225; 324/232; 324/233

[58] Field of Search .......... 324/209, 225–228, 324/232–243, 260, 262

[56] References Cited

U.S. PATENT DOCUMENTS

| | | | |
|---|---|---|---|
| 3,449,664 | 6/1969 | Smith | 324/235 |
| 4,006,407 | 2/1977 | Flaherty et al. | 324/233 |
| 4,041,379 | 8/1977 | Karlsson | 324/260 |
| 4,107,605 | 8/1978 | Hudgell | 324/220 |
| 4,337,431 | 6/1982 | Hale | 324/220 |
| 4,355,281 | 10/1982 | Toth et al. | 324/237 X |
| 4,413,231 | 11/1983 | Amedro et al. | 324/220 |
| 4,467,281 | 8/1984 | Davis et al. | 324/237 X |
| 4,495,587 | 1/1985 | Plante et al. | 324/237 X |
| 4,496,904 | 1/1985 | Harrison | 324/227 |
| 4,507,608 | 3/1985 | Flach et al. | 324/237 X |
| 4,667,149 | 5/1987 | Cohen et al. | 324/64 |
| 4,719,422 | 1/1988 | deWalle et al. | 324/238 |
| 4,739,261 | 4/1988 | Sugiyama et al. | 324/232 |
| 4,745,809 | 5/1988 | Collins et al. | 73/661 |
| 4,747,310 | 5/1988 | Collins et al. | 73/661 |
| 4,761,610 | 8/1988 | Svegander et al. | 324/237 X |
| 4,763,071 | 8/1988 | McGee et al. | 324/236 X |
| 4,821,204 | 4/1989 | Hüschelrath | 324/237 X |
| 4,823,082 | 4/1989 | Nasu et al. | 324/225 X |

FOREIGN PATENT DOCUMENTS

| | | | |
|---|---|---|---|
| 86/01896 | 3/1986 | World Int. Prop. O. | 324/238 |
| 86/02456 | 4/1986 | World Int. Prop. O. | 324/237 |

Primary Examiner—Reinhard J. Eisenzopf
Assistant Examiner—Warren S. Edmonds
Attorney, Agent, or Firm—John D. Lewis; Kenneth E. Walden

[57] ABSTRACT

This invention relates to a method and device for measuring the resistivity of materials. In particular, the methods measure resistivity in carbon fiber reinforced composites as well as any materials with a relative magnetic permeability of 1. The measurement may be made with access restricted to a single side of the material under test.

19 Claims, 4 Drawing Sheets

EDDY CURRENT METHOD FOR MEASURING ELECTRICAL RESISTIVITY AND DEVICE FOR PROVIDING ACCURATE PHASE DETECTION

The invention described herein may be manufactured and used by or for the Government of the United States of America for governmental purposes without the payment of any royalties thereon or therefor.

The present invention relates to the field of nondestructive inspection of materials. In particular, this invention involves methods and a device of eddy current inspection for estimating the electrical resistivity of materials. While the method applies to all materials with a relative magnetic permeability of 1, it is particularly useful when the test material falls in one or more of three categories: (1) the resistivity falls within a range for which there are no calibration standards; (2) only one surface of the test material is accessible; and (3) the resistivity is frequency dependent and must be determined over a particular range of frequencies. It is considered an advantage of the present invention to measure resistivity without electrical contact with the material under test, such as when the material is covered by a protective coating.

BACKGROUND OF THE INVENTION

Carbon fiber reinforced composites (CFRC) are being used to an increasing extent throughout the technological arts. These composites are quickly becoming the material of choice in a wide range of aerospace applications. Their superb strength to weight ratios not only portend use throughout aviation in structural panels, but suggest use in applications such as rocket nozzles on missiles and spacecraft. Likewise, development in submersibles and other pressure structures are turning to these CFRC.

Knowledge of the electrical resistivity of CFRC is necessary to determine their antennae characteristics; to determine their shielding properties; to accurately interpret defect indications in their nondestructive inspection; and to provide quality control during fabrication. A method to interpret defect indications and measure the depth of a defect is taught in an application for U.S. Pat. Ser. No. 294,621 filed January 9th, 1988 by Applicants.

The individual fiber and matrix material components that make up such a composite are often of nonuniform quality and moreover are laminated in different and varied patterns. Additionally, fabricators can be expected to make occasional human errors in the number and spacing of plies in the layup. Slight changes in curing cycles and rates of heating can also have major effects on mechanical properties, but no obvious effect in the visual appearance of the finished parts. In general, the deviation in properties for composite materials on multiple tests is far greater than considered acceptable for established metal technology. Refined and improved nondestructive testing apparatus and methods must be developed to allow inspection to establish, with greater assurance, the exact quality of the part under surveillance.

There are a number of methods available to measure the electrical resistivity (or electrical conductivity) of materials, but all have shortcomings with respect to carbon fiber composite materials. The various contact methods for measuring resistivity are not appropriate for many of these materials because the insulating properties of the matrix material in some classes of CFRC prevent good electrical contact. The existence of coatings also impede measurement in many applications.

Commercially available conductivity meters are designed to measure the nonfrequency dependent conductivity of metals. As a consequence they do not provide conductivity values as a function of frequency and they are applicable only to relatively high conductivities (>1.4% of the International Annealed Copper Standard (IACS)).

Noncontact, through-transmission eddy current methods can provide the necessary measurements, but they are available only in the laboratory and require access to both surfaces of the material. Both surfaces are not always accessible.

Many methods used to measure electrical resistivity require calibration standards. These resistivity standards in the high range of resistivities are not available. The disclosed device and techniques do not require standards.

Collins et al., U.S. Pat. No. 4,747,310 filed May 31, 1988 and Collins et al., U.S. Pat. No. 4,745,809 filed May 24, 1988, use eddy current techniques along with ultrasound and magnetic induction to measure relative conductivity, but teach no method to measure absolute conductivity in thick metal sections or carbon fiber reinforced composites. A knowledge of absolute conductivity is necessary to insure through thickness eddy current inspections; to measure defect depth and to evaluate electromagnetic shielding properties.

The inability to measure the resistivity of very high resistivity materials without providing good electrical contact to the test material, and without providing access to both sides of the test material, is generally recognized in the art. The method and the instrument disclosed herein provide these capabilities.

Therefore, it is an object of this invention to teach a method and device of nondestructive, noncontact measurement of actual (as opposed to relative) electrical resistivity.

It is another object of the instant invention to disclose a method for the measurement of the resistivity of materials whose resistivity is so high that calibration standards do not exist.

It is yet another object of the present invention to teach a method for the measurement of the resistivity of carbon fiber reinforced composites.

It is another object of the invention to teach a method for the measurement of the resistivity of graphite epoxy materials where the epoxy prevents the forming of good electrical contact.

It is yet another object of the present invention to provide a method for the measurement of the electrical resistivity of components when only one surface is accessible.

It is another object to teach a method for detecting variations in fiber density which cause variations in electrical resistivity.

It is another object of the instant invention to teach a method for the measurement of the electrical resistivity of a material over a range of frequencies when the resistivity of the test material is frequency dependent.

It is a further object of the invention to teach a method and instrument which can estimate the resistivity of conducting materials over an unlimited range of resistivities.

It is still another object of the present invention to teach a device for measuring actual resistivity of carbon fiber reinforced composites.

It is still another object of the instant invention to teach a device which exhibits the required frequency and sensitivity to measure resistivity in materials having 50,000 microhm.cm.

It is yet another object of the present invention to provide a device for measuring absolute resistivity having an accuracy over a frequency range adequate to employ the hereinbelow methods.

Other objects, advantages and novel features of the invention will appear from a reading of the following detailed description of the invention when considered in conjunction with the accompanying drawings, wherein:

DETAILED DESCRIPTION OF THE INVENTION

The electrical resistivity of carbon fiber reinforced composites (CFRC) is orders of magnitude higher than that of metals. The high resistivity offers both advantages and disadvantages. On the positive side, it permits eddy current inspection to greater depths than were heretofore associated with eddy current inspection. On the other hand, the resistivities of these materials may differ widely among apparently similar materials. The matrix in many CFRC precludes the formation of the good electrical contact required by contact resistivity measurement methods. The existence of protective coatings also preclude contact, and, in addition, there are no high resistivity standards currently available for the calibration of eddy current probes.

Eddy current nondestructive evaluation, be it defect detection and measurement or resistivity measurement, is based on an analysis of the effect of the test material on the impedance of the eddy current probe. These effects are witnessed by the normalized impedance curve obtained by plotting the normalized imaginary ($X_n$) against the normalized real ($R_n$) components of the impedance. These components are given by $$R_n = (R_m - R_o)/X_o, X_n \text{ and } X_m/X_o$$

where $R_m$ and $X_m$ are the real and imaginary components of the impedance when the probe is in contact with the test material and $R_o$ and $X_o$ are the corresponding values when the probe is in air.

Figure 1:
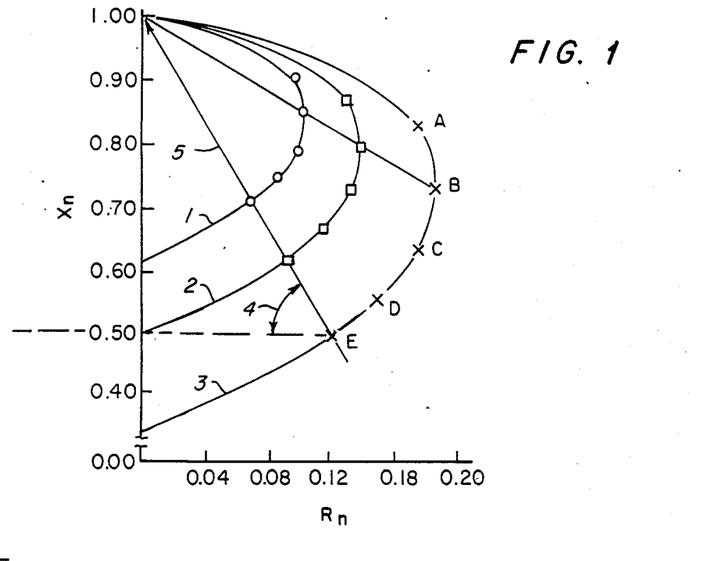
FIG. 1 is a graph illustrating normalized impedance curves.

Turning now to FIG. 1 wherein are shown three normalized impedance curves, labeled 1, 2 and 3, each generated with a different separation (lift-off) between the ferrite cup core probe having an effective radius, r, of 7.11 mm, and a carbon/carbon test material having a resistivity of 840 microhm.cm. Associated with each point on a normalized impedance curve is a reference number given by the dimensionless ratio of the effective radius r, and the skin depth, s. The values of this reference number for points A through E in FIG. 1 are 1.5, 2.2, 3.1, 4.4 and 6.2. Lift-offs associated with curves 1, 2, and 3 are, respectively, 1.32 mm, 0.66 mm and 0.0 mm. The effective radius, r, of the ferrite cup core probe is taken to be one-third of the outside diameter of the core. The relationship of the quantity r to the physical dimensions of other ferrite core geometries is not defined herein.

The lift-off time 5 is the locus of impedances generated as the separation (lift-off) between the probe and the material is increased. Note that this line, connecting points on the three curves which have the same reference number, is straight and intersects the air impedance (1,0).

The shape of a normalized impedance curve refers to its relative extent in the real and imaginary directions. The shape is described by the relationship between the reference number and lift-off angle. All normalized impedance curves generated by ferrite cup-core probes were found to have a characteristic shape, termed herein a universal curve. The characteristic shape pertains when three conditions are met: the skin depth must be less than circa ¾ the thickness of the material; the inductance of the probe must have increased no more than 4% above its minimum value; and there must be no frequency dependent shielding effects.

The universal normalized impedance curve is highly significant. The relationship between lift-off angle 4 and reference number is a property of the probe core design and is insignificantly affected by secondary probe design parameters such as the number and distribution of turns. The product of the probe mean radius and the square root of the frequency can be treated as a normalizing factor. Regardless of the resistivity of the material, any particular point on the curve can be attained by the appropriate selection of the mean probe radius-frequency combination. This feature of the normalized impedance curve is the basis for the method of measuring material resistivity disclosed herein.

For ferrite core probes, there is a linear relationship between the lift-off angle, $\theta_L$ and the reference number. This relationship is given by $$\tan \theta_L = 1 + m (R/S) \qquad 1$$

where $\tan \theta_L$ is the ratio of the change, due to the test material in the normalized imaginary component to the normalized real component, or $$\tan \theta_L = (1 - X_n)/R_n = (X_o - X_m)/(R_m - R_o)$$

where $X_n$ and $R_n$ are the normalized imaginary and real components of the impedance, $X_o$ and $R_o$ are the corresponding components of the impedance of the probe in air, and $X_m$ and $R_m$ are the corresponding components of the impedance of the probe when it is in contact with the test material.

Equation 1 requires that the three conditions cited above be met.

Skin depth, s, in mm, is given by $$s = 50.29 (P/f)^{\frac{1}{2}} \qquad 2$$

where P is the resistivity of the test material and f is the frequency in hertz.

Substitution of equation 2 in equation 1 and solving for resistivity, P, yields:

$$P = m^2 r^2 f / (50.29)^2 (\tan \theta_L - I)^2 \qquad 3$$

When the probe has a ferrite cup core the values of I and m are −0.158 and 0.7035, respectively. Given that the 3 conditions, stated above, are met, the resistivity of any material can be measured. It is only necessary to select the frequency and probe size combination such that the quantity $\tan \theta_L$ is between 0.8 and 6 inclusive. This limitation is not theoretical but practical. Outside of this range, small errors in measurement introduce large errors in the computed quantities.

Figure 6:
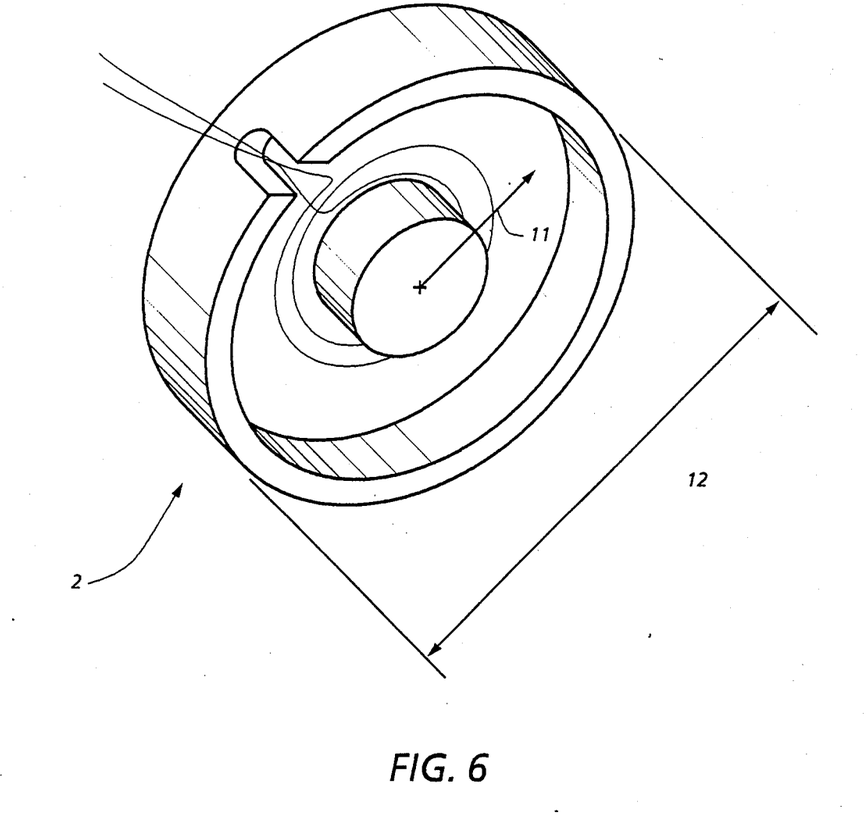
FIG. 6 is a pictorial of an eddy current probe.

Practicality limits the combination of probe size and frequency in combination with material resistivity to values which provide $\tan \theta_L$ values in the range given. There is a further constraint when it is desirable to measure the resistivity of the bulk material, and the resistivity of the material close to the surface is possibly different. This could be the case with some CFRC or with metals where there are oxidation or corrosion products on the surface. In this case the depth over which it is desired to integrate the resistivity measurement determines the smallest probe that can be used. When a ferrite cup core probe is used, the outside diameter should be at least 5 times this depth dimension. The effective radius r is one-third of this outside diameter and therefore, stated another way, the depth dimension should be 1.67 times the radius. Turning to FIG. 6, the radius 11 and the outside diameter 12 of probe 2 may be graphically visualized.

Equation 3 can also be written $$\tan \theta = I + ((mr) f^{\frac{1}{2}} / 50.29)(1/P^{\frac{1}{2}}) \qquad 4$$

The quantity $\tan \theta_L$ can be plotted against $f^{\frac{1}{2}}$. If the probe has a ferrite cup core, these data fall on a straight line whose slope is given by $$S = (mr/50.29)(1/P^{\frac{1}{2}}) \qquad 40$$

since m and r are known, P can be calculated. If the core design is unknown, but if $\tan \theta_L$ versus $f^{\frac{1}{2}}$ is a straight line then the quantity mr can be determined from the slope generated with a material of known resistivity. This quantity can then be used to calculate the resistivity of an unknown material from the slope of the $\tan \theta_L$ versus $f^{\frac{1}{2}}$ curve generated for the material of unknown resistivity.

When the resistivity is unknown and the test material is a thin plate, it is possible that the skin depth may be greater than $\frac{3}{4}$ the thickness of the test material over part of the frequency range. This may also be the case when instrumentation considerations limit the maximum frequencies that can be achieved. For example, even with only a single turn, the resonant frequency of a ferrite core probe may prevent its effective use in the frequency range demanded by the resistivity and thickness of the test material.

Resistivity values calculated for frequencies in the lower portion of the frequency range, or possible over the entire range, will tend to be high if, at those frequencies, the skin depth is greater than $\frac{3}{4}$ the thickness of the test material. When frequencies are such that the skin depth is less than $\frac{3}{4}$ the thickness of the test material the calculated resistivity values scatter about a median value representing the resistivity of the test material to within plus or minus 10%. If the calculated resistivity values continue to decrease with increasing frequency, never reaching a constant value, it can be assumed that over the entire frequency range the skin depth was too great.

If the instrumentation, including the probe design, is such that the necessary high frequencies cannot be achieved, a second relationship can be used:

$$P_E^{3/2} + C_1 P_E + C_2 P_E^{\frac{1}{2}} + C_3 = 0 \qquad 5$$

where
$C_1 = f^{\frac{1}{2}}(AT - Br)/(\tan \theta_L + C)$
$C_2 = fT(Dr + ET)/(\tan \theta_L + C)$
$C_3 = GrT^2 f^{3/2}/(\tan \theta_L + C)$ where r is a linear dimension, in mm, related to the physical dimensions of the probe core, T is the thickness, in mm, of the test material, f is the frequency in hertz, the constants A,B,C,D,E, and G are constants determined by the geometry of the ferrite core of the probe, and $\tan \theta_L$ is the tangent of lift-off angle. $P_E$ is the resistivity of the test material when conditions are such that the skin depth is greater than $\frac{3}{4}$ the thickness of the test material. Equation 5 can be solved for $P_E$ by a method of successive approximation.

When the probe has a ferrite cup core, r is equal to $\frac{1}{3}$ the outside diameter of the core and the constants are A=0.0808, B=0.0526, C=0.023, D=0.1817, E=0.112, and G=0.025.

Of course, it is not necessary to use a multifrequency approach. If the resistivity can be assumed with confidence to be such that skin depth at a specific frequency is less than $\frac{3}{4}$ the thickness of the test material, equation 4 can be used. The data collected at that single frequency can be used to calculate the resistivity. By the same token, if the resistivity can be assumed with confidence to be such that the skin depth at a specific frequency is greater than the thickness of the test material, equation 5 can be used to calculate the resistivity. To reduce the effects of scatter the single frequency measurements can be repeated several times and averaged.

Figure 2:
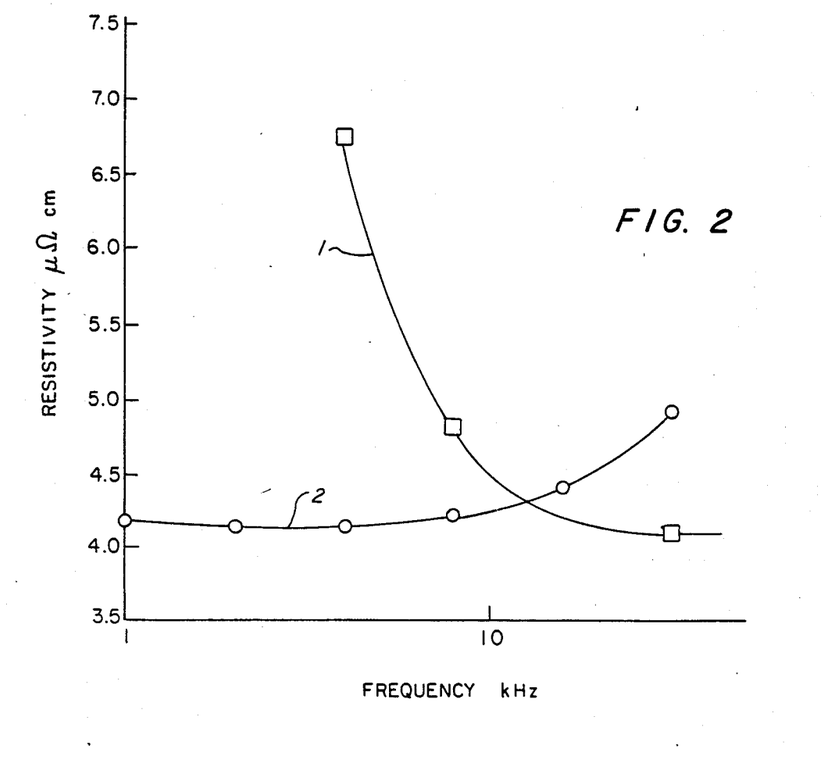
FIG. 2 is a graph of calculated resistivities for aluminum.

When conditions are such that it cannot be assumed that only equation 4 or only equation 5 are applicable, resistivities can be calculated using both equations. When the calculated resistivities, P and $P_E$ are plotted against frequency the actual resistivity of the material can be discerned. Turning now to FIG. 2 wherein are plotted both P, curve 1, and $P_E$, curve 2, against log frequency. The material was a 1.27 mm thick aluminum plate having a resistivity of 4.1 microhm.cm. The calculated values of $P_E$ are constant, with some scatter, with frequency between 1 and 8 KHz. In this frequency range the skin depth varies from 2.5 times the thickness of the test material to 0.9 the thickness. Over this same range, P values are decreasing with frequency. The $P_E$ and P curves cross at the frequency where the skin depth is $\frac{3}{4}$ the thickness. At frequencies above this crossover point, for example at 16 KHz and at 32 KHz, P values are constant with frequency and $P_E$ values increase. An average of the data points which scatter about the straight line provides an accurate measure of the resistivity. The resistivity would also be calculated by assuming that, at the crossover frequency, the resistivity is such that the skin depth is equal to $\frac{3}{4}$ the thickness of the test material.

The structure of graphite epoxy requires the use of a correction factor, H. In equations 4 and 5, the geometric quantities (r and T) must be multiplied by this factor. An effective value of this factor for ferrite cup core probes is 1.414, although slight variations in this factor are acceptable without departing from the scope of Applicants' invention.

The resistivity of some graphite epoxy materials can be frequency dependent. It is generally constant with frequency from DC to some frequency where it begins to increase before again leveling off. If the resistivity of the test material increases over the frequency range where the skin depth/thickness ratio is greater than 0.75 then the calculated values of $P_E$ are not level, but also increase with frequency. Since the calculated values of P are decreasing over this range, it can be assumed that the crossover point has not been reached and, consequently, the calculated value of $P_E$, at each frequency, is the resistivity of the test material at that frequency.

Figure 3:
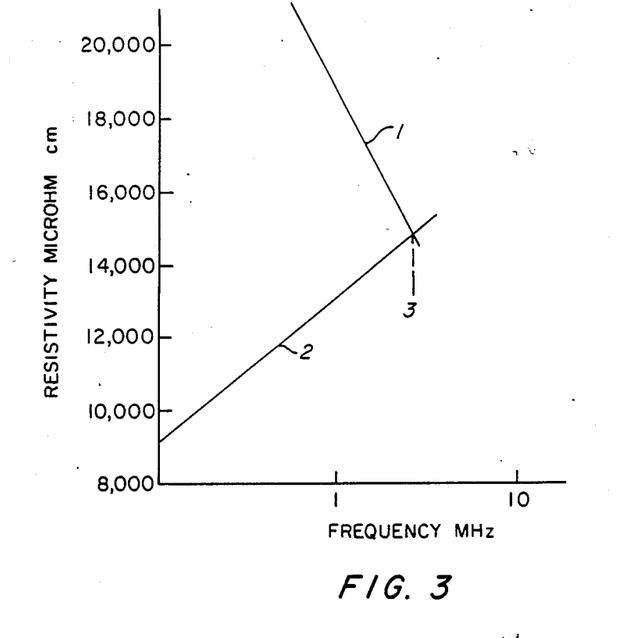
FIG. 3 is a graph of calculated resistivities for graphite epoxy.

These effects are illustrated in FIG. 3 wherein are plotted the calculated values of P (curve 1) and $P_E$ (curve 2) for a graphite epoxy whose resistivity was frequency dependent. The curves cross at 6 MHz (point 3) where the estimated resistivity was 15,000 microhm.cm and the skin depth was $\frac{3}{4}$ the thickness of the material.

When the resistivity of such a material is measured over a higher frequency range, where the skin depth/thickness ratio is less than 0.75, then both P and $P_E$ increase with frequency. It is obvious the frequency is above the crossover point and the values of P, calculated at each frequency, is the resistivity of the test material at the frequency.

In summary, both P and $P_E$ can be plotted against frequency and the frequency at which the two curves cross (crossover point) identified. At frequencies below this point the value of $P_E$ calculated at each frequency is the resistivity of the test material at that frequency. At frequencies above the crossover point, the value of P, calculated at each frequency, is the resistivity of the test material at that frequency.

The entire method, including selection of appropriate values, can be implemented in software so the method is transparent to the technician.

Figure 4:
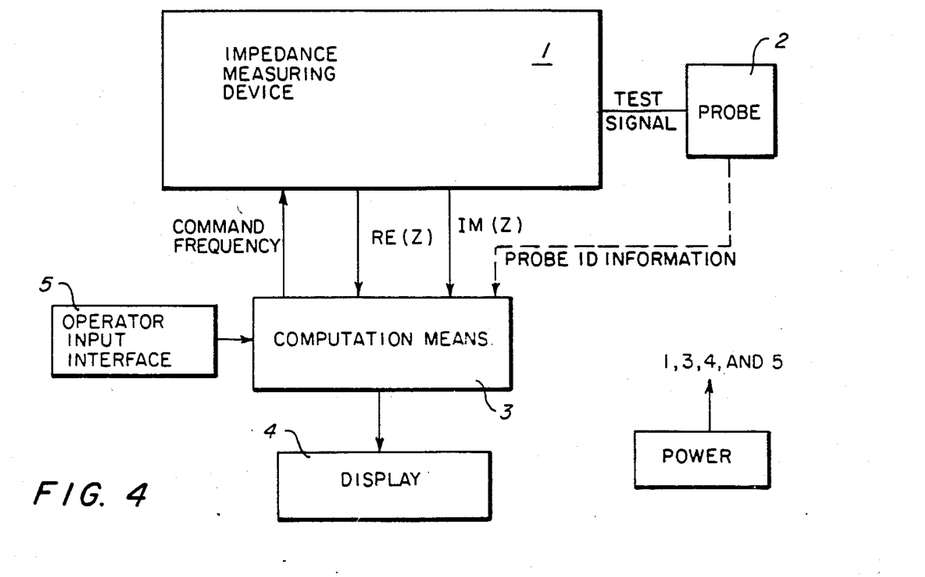
FIG. 4 is a block system diagram of a resistivity measuring device.

A resistivity measuring device to perform the above techniques can be constructed by commercially available electronic components once the herein disclosed methods are known. FIG. 4 is a block diagram of one such instrument. Therein, a means for measuring impedance 1, capable of accurate measurement of the impedance of an eddy current probe 2 over a wide range of frequencies is shown. The impedance measuring device 1 may be an impedance analyzer, a precision bridge circuit, or a hetrodyne circuit, as long as the circuitry is capable of measuring the absolute impedance over a wide frequency range covering at least 10 KHz to 50 MHz.

Probe 2 must be one of a set capable of operating over a frequency range adequate to fully apply the methods above to the material of interest. The means for measuring impedance 1 of FIG. 4 should also be capable of measuring over the same frequency range. This probe will be preferably of the ferrite cup core type and physically much larger than those generally associated with the eddy current inspection art.

The impedance measuring device 1 is in electrical connection with a means for computation 3. The means for computation must accept the probe impedance measurements in air and on the test material and be capable of performing the algorithms and calculations required for performing the herein disclosed methods. Computation means 3 may be an electrical interface with probe 2 or the operator can manually insert the probe parameters. This could be automatically accomplished by electrical identifiers on each probe.

This computation means can be a microprocessor or discrete logic circuits. A display 4 is connected to the computation means 3 whereby the resistivity values may be discerned by an operator. It is worthy to note that probe 2 will vary in size depending upon the depth over which it is desired to integrate the resistivity measurement. It is anticipated that a field device of comprehensive scope will have several probes available. Finally, an operator input interface 5 such as a keypad or control panel allows the operator to signal the computation means 3 whether the probe is in air or on the test material, the probe selected if not determined automatically by probe connectors, and information about the test material.

In addition to performing the required calculations and algorithms, computation means 3 will also command the means for measuring impedance 1 to operate at the appropriate frequencies. In the preferred embodiment the device of FIG. 4 will have a power supply 6 that will be battery powered. The device should also be lightweight to allow field testing such as would be needed on a flight line.

Figure 5:
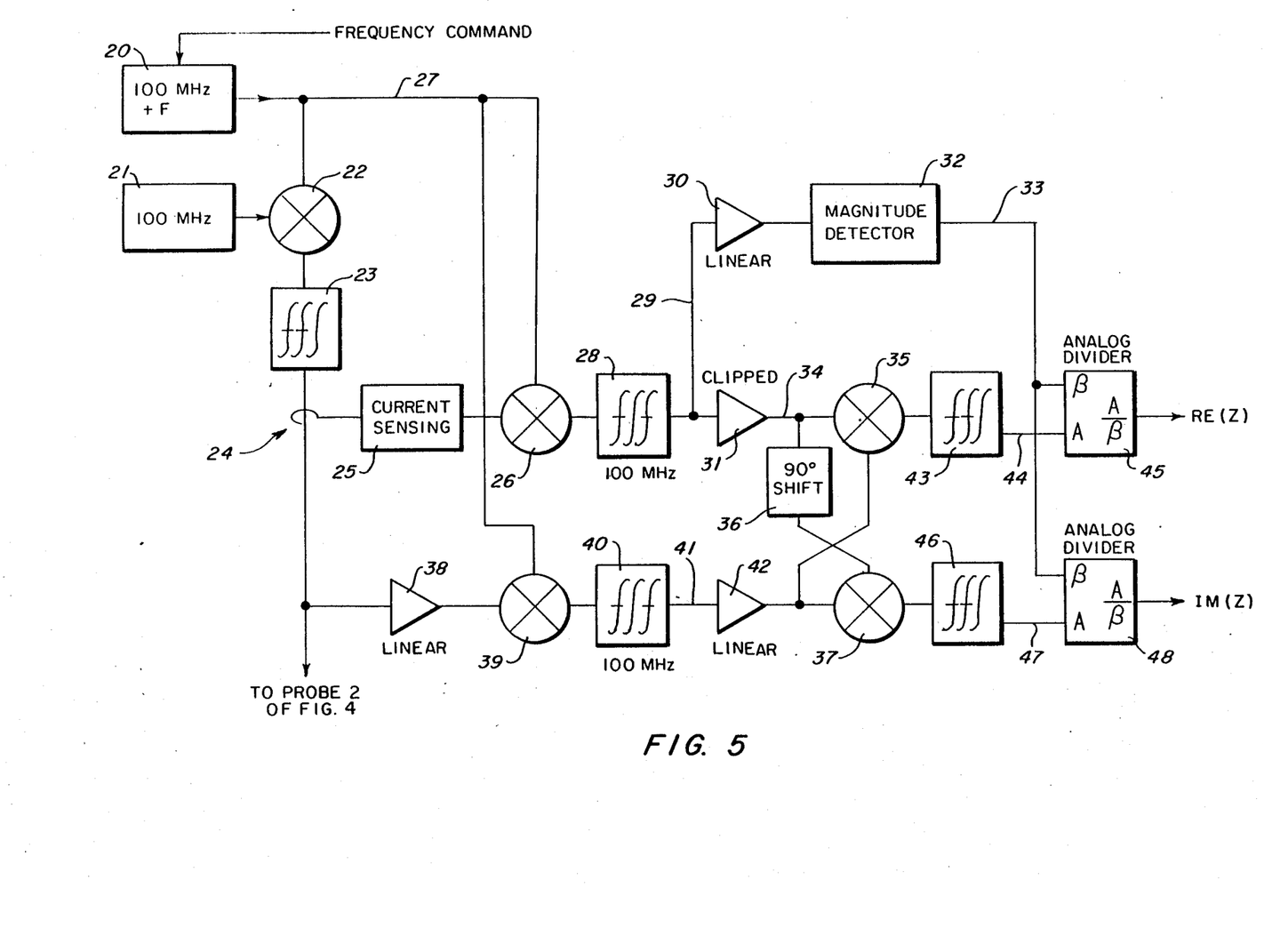
FIG. 5 is a block circuit diagram of a means for measuring impedance of the resistivity measuring device of FIG. 4.

The means for measuring impedance 1 of FIG. 4 must provide capability of measurement over a wider range of frequencies and be able to measure lower impedance values than eddy current systems currently in the art. This capability may be obtained by various electronic methods. One such method is illustrated in FIG. 5 wherein a block diagram of an electrical circuit capable of the frequencies and sensitivities required, is disclosed. It is considered to be the preferred embodiment to use a hetrodyne technique such as illustrated in FIG. 5 in order to provide the required accuracy in phase detection over a wide range of frequencies. This hetrodyne technique is generally not used in currently available eddy current systems although laboratory instruments are known to hetrodyne.

Continuing with FIG. 5, a frequency source 20 provides a variable frequency as required. This frequency is higher than the desired eddy current test frequency by a fixed amount related to a chosen intermediate frequency (IF) which is 100 MHz in this embodiment. 21 provides this 100 MHz IF frequency, which is used to down convert the output of frequency source 20 by means of mixer 22 and filter 23 which is a low pass device. The output of low pass filter 23 is fed to an appropriate probe 2 via an interconnecting line 24. A current sensing circuit 25 monitors current flow in line 24 and outputs a proportional voltage to a second mixer 26. Mixer 26 hetrodynes the signal from current sensing device 25 with the frequency source on line 27 which arrives from 20. The output of mixer 26 is passed through a 100 MHz IF filter 28 where it is fed via line 29 to amplifier 30. Filter 28 also outputs the signal on line 29 to a clipping amplifier 31. It is important to note that the signal fed from filter 28 to amplifiers 30 and 31 is a signal at the chosen IF frequency with an amplitude proportional to the current into probe 2 and a phase (at 100 MHz) in fixed relation with the phase of the current into probe 2. Linear amplifier 30 outputs a signal to a magnitude detector 32 which in turn provides a dc signal on line 33 proportional to the magnitude of current fed to probe 2.

The output of amplifier 31 provides a reference signal 34 corresponding to the phase of the signal fed to probe 2. Signal 34 is a reference input to mixer 35 discussed hereinbelow. Signal 34 also is fed to a 90° phase shifting circuit 36 where it is phase shifted and outputted to mixer 37 as a reference.

Amplifier 38 senses the voltage across probe 2 and outputs a signal proportional to that voltage to mixer 39 wherein it is mixed with the signal from line 27. Output of mixer 39 is passed through band pass filter 40 where the output is a 100 MHz signal on line 41 whose amplitude is proportional to the amplitude of the voltage across probe 2 with a phase proportional to the phase of that voltage. This signal on line 41 is received and amplified by linear amplifier 42 where it is outputted to mixers 35 and 37.

Mixer 35 outputs a signal through low pass filter 43 which is a signal proportional to the in-phase component of the voltage across the probe and outputted on line 44. It should be noted that the signal on line 44 is proportional to the component of the voltage across probe 2 that is in phase with probe current. This signal of line 44 is fed to an analog divider device 45 wherein the voltage from line 44 is divided by the voltage from line 33 giving the resultant output which is the real component of the impedance of probe 2.

Similarly, the output of mixer 37 is filtered in low pass filter 46 which becomes an input to analog divider 48 on line 47. This produces an output from divider 48 which is the imaginary component of the impedance of probe 2.

Therefore, this basic device is capable of measuring all impedance values necessary to perform the methods resulting in a value equal to the actual resistivity of a material including those constructed from CFRC.

Modifications and variations of the present methods and device are possible in light of the above teachings and within the purview of the appended claims without departing from the spirit and scope of the invention.

We claim:

1. A method for determining the electrical resistivity of a material via the effect of the material on the lift-off angle of a ferrite core eddy current probe comprising the following steps:
   (a) providing an electrically conductive nonmagnetic material to be tested; then
   (b) selecting a probe of effective radius r that is at least 1.67 times the thickness of said material over which resistivity measurements are desired; then
   (c) connecting the probe of said step (b) to a means for measuring impedance having a range of frequencies; then
   (d) selecting on the impedance measuring device of said step (c) a range of frequencies such that $\tan \theta$ falls between 0.8 and 6; then
   (e) measuring over the frequency range selected in said step (d) the imaginary ($X_o$) and real ($R_o$) components of the impedance with the probe selected in said step (b) in air; then
   (f) storing the data obtained in said step (e); then
   (g) measuring over said selected frequency range the real ($R_m$) and imaginary ($X_m$) components of the impedance of the probe of said step (b) when the probe is in contact with the material of said step (a); then
   (h) calculating over said selected frequency range the tan of the lift-off angles according to $\tan \theta_L = (X_o - X_m)/(R_m - R_o)$; then (i) substituting each value of $\tan \theta_L$ in said step (h) into the relationship $P = m^2 r^2 f/(50.29)^2 (\tan \theta_L - I)^2$ where m and I are constants which depend on the shape of the ferrite core and which have been empirically determined, using a material of known resistivity, by plotting $\tan \theta$ versus $rf^{\frac{1}{2}}/50.29 \, p^{\frac{1}{2}}$, and r is the effective radius of the probe selected in said step (b) and f is the frequency in hertz; then
   (j) storing the resultant values obtained in said step (i); and
   (k) substituting each value of $\tan \theta_L$ calculated in said step (h) into the relationship $$P_E^{3/2} + C_1 P_E + C_2 P_E^{\frac{1}{2}} + C_3 = 0$$

where
   $C_1 = f^{\frac{1}{2}}(AT - Br)/(\tan \theta_L + C)$
   $C_2 = fT(Dr + ET)/(\tan \theta_L + C)$
   $C_3 = GrT^2 f^{3/2}/(\tan \theta_L + C)$
   and where the constants, A,B,C,D,E and G depend on core geometry and have been determined empirically using material of known resistivity and thickness, and r in millimeters is the effective radius of the probe selected in said step (b), T is the thickness (in mm) of the material provided at said step (a), f is the frequency in hertz; and $P_E$ is the resistivity of the test material of said step (a) under conditions where the skin depth is greater than the thickness of the test material, solving for $P_E$; then
   (l) selecting from the values of P at said step (i) and the values of $P_E$ at said step (k) those values which appear to be randomly distributed about a means; then
   (m) averaging the values at said step (l) to determine the resistivity of the material.

2. A method according to claim 1 wherein the probe selected in said step (b) has a ferrite cup core; and in step (i) M = 0.7035, I = -0.158 and r = ⅓ the outside diameter (in mm) of the ferrite core; and at step (k) the constants are A = 0.0808, B = 0.0526, C = 0.023, D = 0.1817, E = 0.112, G = 0.025 and r is equal to the value of r in said step (i).

3. A method for determining the resistivity of a nonmagnetic material of such thickness that this dimension does not affect the eddy current measurements, comprising the following steps:
   (a) providing an electrically conducting nonmagnetic material of sufficient thickness, to be tested, then
   (b) selecting a probe of effective radius r that is at least 1.67 times the thickness of said material over which resistivity measurements are desired; then
   (c) connecting the probe of said step (b) to a means for measuring impedance having a range of frequencies; then
   (d) selecting on the impedance measuring device of said step (c) a range of frequencies such that $\tan \theta$ falls between 0.8 and 6; then
   (e) measuring over the frequency range selected in said step (d) the imaginary ($X_o$) and real ($R_o$) components of the impedance with the probe selected in said step (b) in air; then
   (f) storing the data obtained in said step (e); then
   (g) measuring over said selected frequency range the real ($R_m$) and imaginary ($X_m$) components of the impedance of the probe of said step (b) when the probe is in contact with the material of said step (a); then (h) calculating over said selected frequency range the tan of the lift-off angles according to tan $\theta_L = (X_o - X_m)/(R_m - R_o)$; then (i) substituting each value of tan $\theta_L$ in said step (h) into the relationship $P = m^2 r^2 f/(50.29)^2 (\tan \theta_L - I)^2$ where m and I are constants which depend on the shape of the ferrite core and which have been empirically determined, using a material of known resistivity, by plotting tan $\theta$ versus $rf^{\frac{1}{2}}/50.29 P^{\frac{1}{2}}$, and r is the effective radius of the probe selected in said step (b) and f is the frequency in hertz; then (j) averaging the values of said step (i) to determine the resistivity of the material.

4. A method according to claim 3 wherein the probe selected in said step (b) has a ferrite cup core; and in step (i) $M = 0.7035$, $I = -0.158$, and $r = \frac{1}{3}$ the outside diameter of the core.

5. A method for determining the electrical resistivity of a nonmagnetic material via the effect of the material on the lift-off angle of a ferrite core eddy current probe comprising the steps:

(a) providing an electrically conductive material to be tested of such thickness that this dimension does not effect the eddy current measurement; then (b) selecting a probe of effective radius r that is at least 1.67 times the thickness of said material over which resistivity measurements are desired; then (c) connecting the probe of said step (b) to a means for measuring impedance having a range of frequencies; then (d) selecting a single frequency on the means for measuring impedance of said step (c) such that tan $\theta$ is equal to or greater than 0.8 and less than or equal to 6; then (e) measuring at the frequency range selected in said step (d) the imaginary ($X_o$) and real ($R_o$) components of the impedance with the probe selected in said step (b) in air; then (f) storing the data obtained in said step (c); then (g) measuring over said selected frequency range the real ($R_m$) and imaginary ($X_m$) components of the impedance of the probe of said step (b) when the probe is in contact with the material of said step (a); then (h) calculating at said selected frequency the tan of the lift-off angles according to tan $\theta_L = (X_o - X_m)/(R_m - R_o)$; then (i) substituting the value of tan $\theta_L$ at said step (h) into the relationship $P = m^2 r^2 f/(50.29)^2 (\tan \theta_L - I)^2$ where m and I depend on core geometry and have been determined empirically using material of known resistivity and thickness, and r in millimeters is the effective radius of the probe selected in said step (b) and f is the frequency in hertz; and solving for P, the resistivity of the material.

6. A method according to claim 5 further defined by: selecting a ferrite cup core probe in said step (b); and at said step (i) the value of the constants are $M = 0.7035$, $I = -0.158$ and r in mm is $\frac{1}{3}$ the outside diameter of the core of the probe selected at said step (b).

7. A method for determining the electrical resistivity of graphite epoxy via the effect of the graphite epoxy on the lift-off angle of a ferrite core eddy current probe comprising the following steps:

(a) providing a graphite epoxy material to be tested;

(b) selecting a probe of effective radius r that is at least 1.67 times the thickness of said material over which resistivity measurements are desired; then (c) connecting the probe of said step (b) to a means for measuring impedance having a range of frequencies; then (d) selecting on the impedance measuring device of said step (c) a range of frequencies such that tan $\theta$ falls between 0.8 and 6; then (e) measuring over the frequency range selected in said step (d) the imaginary ($X_o$) and real ($R_o$) components of the impedance with the probe selected in said step (b) in air; then (f) storing the data obtained in said step (e); then (g) measuring over said selected frequency range the real ($R_m$) and imaginary ($X_m$) components of the impedance of the probe of said step (b) when the probe is in contact with the material of said step (a); then (h) calculating over said selected frequency range the tan of the lift-off angles according to tan $\theta_L = (X_o - X_m)/(R_m - R_o)$; then (i) substituting each value of tan $\theta_L$ calculated in step (h) into the equation $$P = H^2 m^2 r^2 f/(50.29)^2 (\tan \theta_L - I)^2$$

where P is the resistivity of the graphite epoxy under conditions where the skin depth is less than $\frac{3}{4}$ the thickness of the graphite epoxy, $H = 1.414$, the values of the constants m and I are constants which depend on the shape of the ferrite core of the probe selected at said step (b) and which have been empirically determined using a material of known resistivity, by plotting tan $\theta$ versus $rf^{\frac{1}{2}}/50.29 P^{\frac{1}{2}}$, and r, (in mm) is the effective radius of the core of said probe selected in said step (b), and f is the frequency in hertz; then (j) storing the resultant values obtained in said step (i); and (k) substituting each value of tan $\theta_L$ obtained at said step (h) into the equation $$P_E^{3/2} + C_1 P_E + C_2 P_E^{\frac{1}{2}} + C_3 = 0$$

where
$C_1 = H f^{\frac{1}{2}} (AT - Br)/\tan \theta_L + C)$
$C_2 = H^2 T f (Dr + ET)/\tan \theta_L + C)$
$C_3 = H^3 r T^2 f^{3/2} G/(\tan \theta_L + C)$
and where the constants A, B, C, D, E and G depend on core geometry and have been determined empirically using material of known resistivity and thickness, and r in mm is the effective radius of the probe selected at said step (b), T (in mm) is the thickness of the material provided at said step (a), f is the frequency in hertz, $H = 1.414$, and $P_E$ is the resistivity of the test material provided at said step (a) under conditions where the skin depth is greater than the thickness of the test material, solving for $P_E$; then (l) plotting both the values of P calculated at said step (i) and the values of $P_E$ calculated at said step (k) against frequency and identifying the frequency where the 2 curves cross, identified as the crossover point; then (m) taking the value of $P_E$ calculated at each frequency below the crossover point as the resistivity of the test material at that frequency and taking the value of P calculated at each frequency above the crossover point as the resistivity of the test material at that frequency.

8. A method for determining the electrical resistivity of graphite epoxy via the effect of the graphite epoxy on the lift-off angle of a ferrite core eddy current probe comprising the following steps;
   (a) providing a graphite epoxy material to be tested that has a thickness such that the thickness does not effect the eddy current measurement; then
   (b) selecting a probe of effective radius r that is at least 1.67 times the thickness of said material over which resistivity measurements are desired; then
   (c) connecting the probe of said step (b) to a means for measuring impedance having a range of frequencies; then
   (d) selecting a single frequency on the means for measuring ilmpedance of said step (c) such that tan $\theta$ is equal to or greater than 0.8 and less than or equal to 6; then
   (e) measuring at the frequency selected in said step (d) the imaginary ($X_o$) and real ($R_o$) components of the impedance with the probe selected in said step (b) in air; then
   (f) storing the data obtained in said step (e); then
   (g) measuring over said selected frequency range the real ($R_m$) and imaginary ($X_m$) components of the impedance of said step (b) when the probe is in contact with the material of said step (a); then
   (h) calculating at said selected frequency the tan of the lift-off angles according to tan $\theta_L = (X_o - X_m)/R_n - R_o)$; then
   (i) substituting each value of tan $\theta_L$ obtained at said step (h) into the equation $$P_E^{3/2} + C_1 P_E + C_2 P_E^{\frac{1}{2}} + C_3 = 0$$

where
$C_1 = Hf^{\frac{1}{2}}(AT - Br)/\tan \theta_L + C)$
$C_2 = H^2 Tf(Dr + ET)/(\tan \theta_L + C)$
$C_3 = H^3 r T^2 f^{3/2} G/(\tan \theta_L + C)$
and where the constants A, B, C, D, E, and G are constants empirically determined using material of known resistivity and thickness and r (in mm) is the mean radius of the probe selected at said step (b), T (in mm) is the thickness of the material provided at said step (a), f is the frequency in hertz, H = 1.414, and $P_E$ is the resistivity of the test material provided at said step (a) at the frequency selected at step (d), solving for $P_E$.

9. A method according to claim 7 wherein the probe selected in said step (b) has a ferrite cup core; and at
   step (i) m = 0.7035, I = -0.158 and r = ⅓ the outside diameter of the core in mm, and at
   said step (k) r is as given in said step (i), and A = 0.0808, B = 0.0526, C = 0.223, D = 0.1817, E = 0.112 and G = 0.025.

10. A method according to claim 8 further defined by: selecting a ferrite cup core probe at said step (b); and at
    said step (i) the value of the constants are A = 0.0808, B = 0.0526, C = 0.023, D = 0.1817, E = 0.112, G = 0.025 and r in mm is equal to ⅓ the outside diameter of the core of the probe selected at said step (b).

11. A method according to claim 7 wherein: the value of H in said steps (i) and (k) is some number between 1.3 and 1.5.

12. A method according to claim 8 wherein: the value of H in said step (i) is some number between 1.3 and 1.5.

13. A method according to claim 9 wherein: the value of H in said steps (i) and (k) is some number between 1.3 and 1.5.

14. A method according to claim 10 wherein: the value of H in said step (i) is some number between 1.3 and 1.5.

15. A method for determining the resistivity of a nonmagnetic material of such thickness that this dimension does not affect the eddy current measurements comprising the steps:
    (a) providing an electrically conductive nonmagnetic material of such thickness that this dimension does not effect the eddy current measurement; then
    (b) selecting a probe of effective radius r that is at least 1.67 times the thickness of said material over which resistivity measurements are desired; then
    (c) connecting the probe of said step (b) to a means for measuring impedance having a range of frequencies; then
    (d) selecting on the impedance measuring device of said step (c) a range of frequencies such that tan $\theta$ falls between 0.8 and 6; then
    (e) measuring over the frequency range selected in said step (d) the imaginary ($X_o$) and real ($R_o$) components of the impedance with the probe selected in said step (b) in air; then
    (f) storing the data obtained in said step (e); then
    (g) measuring over said selected frequency range the real ($R_m$) and imaginary ($X_m$) components of the impedance of the probe of said step (b) when the probe is in contact with the material of said step (a); then
    (h) calculating over said selected frequency range the tan of the lift-off angles according to tan $\theta_L = (X_o - X_m)/(R_m - R_o)$; then
    (i) plotting those values of tan $\theta_L$ selected at said step (h) against the square root of frequency; then
    (j) calculating the slope, S of the curve plotted at said step (j); then
    (k) substituting the value of S at said step (j) into the equation $$P = (mr/50.29S)^2$$

where r is the effective radius of the ferrite core selected at said step (b) and m is a constant which depends on the geometry of said core, and which has been empirically determined using a material of known resistivity and P is the resistivity of the material provided at said step (a).

16. A method according to claim 15 wherein at said step (b) the probe selected has a ferrite cup core; and at step (k) r, in mm, is equal to ⅓ the outside diameter of the core selected at said step (b) and the value of m is 0.7035.

17. An eddy current device for determining resistivities in conductive materials comprising:
    a means for measuring absolute impedance capable of measuring impedance over a wide range of frequencies; in electrical connection with
    an eddy current probe of effective radius r that is at least 1.67 times the thickness of said material over which resistivity measurements are desired; and a computation means in electrical connection with said impedance measuring device; outputting signals to a means for inputting command signals in electrical connection with said computation means.

18. An eddy current device according to claim 17 wherein said means for measuring absolute impedance employs heterodyne techniques.

19. An eddy current device according to claim 18 wherein said means for measuring absolute impedance has an operating range of 10 KHz to 50 MHz.

* * * * *